United States Patent
Fang et al.

(10) Patent No.: US 10,919,837 B2
(45) Date of Patent: Feb. 16, 2021

(54) PRODUCTION OF AMINES UTILIZING ZEOLITE CATALYSTS

(71) Applicant: RHODIA OPERATIONS, Paris (FR)

(72) Inventors: Lin Fang, Shanghai (CN); Zhen Yan, Shanghai (CN); Javier Diaz-Maroto Carpintero, Shanghai (CN)

(73) Assignee: RHODIA OPERATIONS, Aubervilliers (FR)

( * ) Notice: Subject to any disclaimer, the term of this patent is extended or adjusted under 35 U.S.C. 154(b) by 56 days.

(21) Appl. No.: 16/083,594

(22) PCT Filed: Mar. 10, 2017

(86) PCT No.: PCT/CN2017/076241
§ 371 (c)(1),
(2) Date: Sep. 10, 2018

(87) PCT Pub. No.: WO2017/152868
PCT Pub. Date: Sep. 14, 2017

(65) Prior Publication Data
US 2019/0071389 A1    Mar. 7, 2019

(30) Foreign Application Priority Data

Mar. 11, 2016   (CN) .............................. 2016/076107

(51) Int. Cl.
*C07C 209/16* (2006.01)
*B01J 23/755* (2006.01)
(Continued)

(52) U.S. Cl.
CPC .......... *C07C 209/16* (2013.01); *B01J 23/462* (2013.01); *B01J 23/755* (2013.01); *B01J 29/084* (2013.01); *B01J 29/106* (2013.01); *B01J 29/126* (2013.01); *B01J 29/22* (2013.01); *B01J 29/24* (2013.01); *B01J 29/44* (2013.01); *B01J 29/46* (2013.01); *B01J 29/7007* (2013.01); *B01J 29/7407* (2013.01); *B01J 29/7415* (2013.01);
(Continued)

(58) Field of Classification Search
None
See application file for complete search history.

(56) References Cited

U.S. PATENT DOCUMENTS 3,384,667 A    5/1968  Hamilton
4,082,805 A    4/1978  Kaeding
(Continued)

FOREIGN PATENT DOCUMENTS

CN    1869001 A    11/2006
WO    2014059574 A1    4/2014

OTHER PUBLICATIONS

English Machine Translation of Chao et al. (CN 1869001) (Year: 2007).*

(Continued)

*Primary Examiner* — Sudhakar Katakam
*Assistant Examiner* — Jennifer C Sawyer

(57) ABSTRACT

The present invention concerns a process for forming a primary or a secondary amine via amination reaction comprising: reacting an alcohol with an amine in the presence of a zeolite comprising a transition metal chosen in the group consisting of Group 8 to 12 elements of the Periodic Table and any combination thereof.

15 Claims, 1 Drawing Sheet

(51) Int. Cl.
*B01J 29/70* (2006.01)
*B01J 23/46* (2006.01)
*B01J 29/08* (2006.01)
*B01J 29/74* (2006.01)
*B01J 37/02* (2006.01)
*B01J 29/10* (2006.01)
*B01J 29/12* (2006.01)
*B01J 29/22* (2006.01)
*B01J 29/24* (2006.01)
*B01J 29/44* (2006.01)
*B01J 29/46* (2006.01)
*B01J 29/76* (2006.01)
*C07C 209/18* (2006.01)
*C07C 211/03* (2006.01)
*C07C 211/09* (2006.01)
*C07C 211/26* (2006.01)

(52) U.S. Cl.
CPC ....... *B01J 29/7615* (2013.01); *B01J 37/0201* (2013.01); *C07C 209/18* (2013.01); *C07C 211/03* (2013.01); *C07C 211/09* (2013.01); *C07C 211/26* (2013.01)

(56) References Cited

U.S. PATENT DOCUMENTS

| | | | |
|---|---|---|---|
| 4,503,023 A | 3/1985 | Breck et al. | |
| 4,918,234 A | 4/1990 | Deeba | |
| 5,917,092 A * | 6/1999 | Vedage | C07C 209/16 564/480 |
| 2004/0199017 A1 | 10/2004 | Ding | |
| 2010/0274056 A1 | 10/2010 | Fukushima et al. | |

OTHER PUBLICATIONS

Human English Translation of Chen et al. (CN 1869001), 2006.*
Kaduk, et al., "Crystal Structure of Zeolite As a Function of Ion Exchange", The Rigaku Journal, 1995, vol. 12, No. 2, pp. 14-34.
Sara Zamanian et al., "N-alkylation of Amines by Ruthenium Supported on Mordenite and Y Zeolite", Current Catalysis, 2014, vol. 3, pp. 65-72.

* cited by examiner

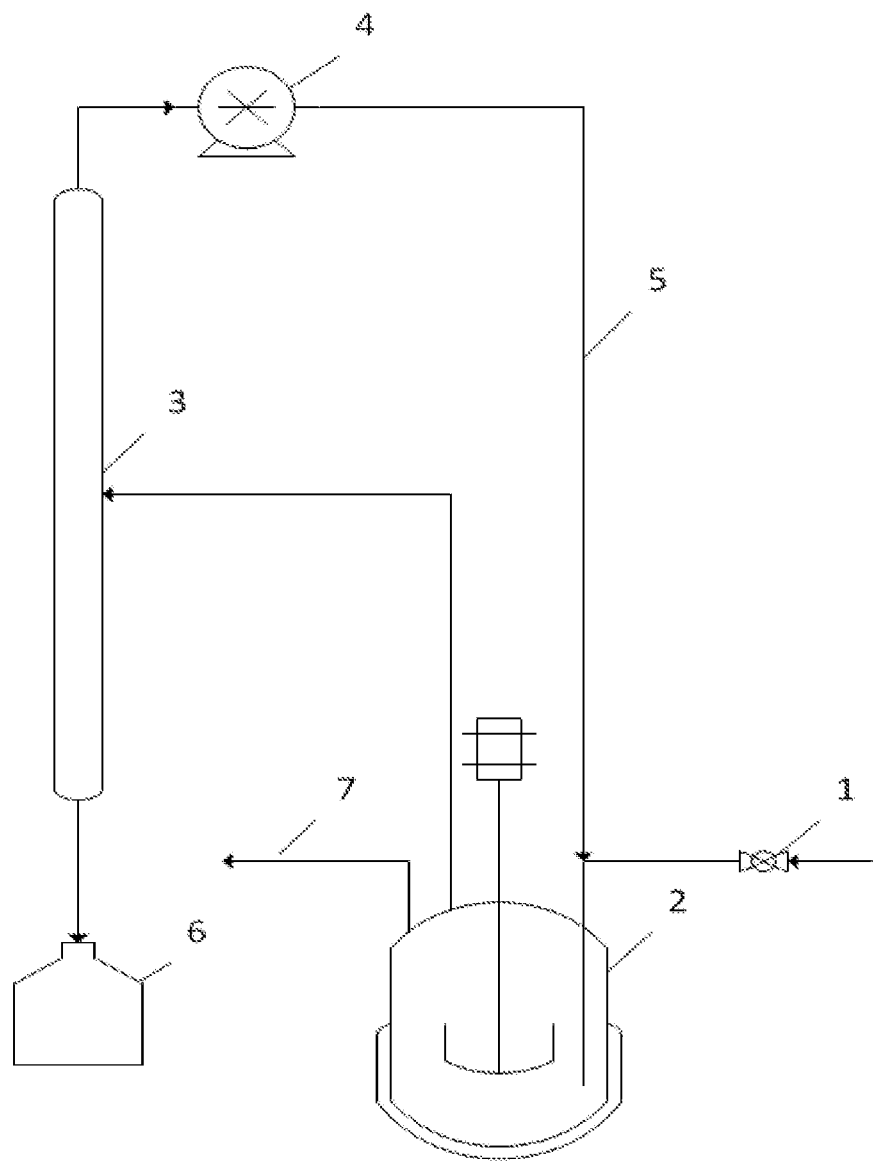

PRODUCTION OF AMINES UTILIZING ZEOLITE CATALYSTS

CROSS-REFERENCE TO RELATED APPLICATION

This application is a U.S. national stage entry under 35 U.S.C. of International Application No. PCT/CN2017/076241 filed Mar. 10, 2017, which claims priority to International Application No. PCT/CN2016/076107 filed Mar. 11, 2016. The entire contents of these applications are explicitly incorporated herein by this reference.

TECHNICAL FIELD

The present invention concerns a process for forming a primary or a secondary amine via amination reaction comprising: reacting an alcohol with an amine in the presence of a zeolite comprising a transition metal chosen in the group consisting of Group 8 to 12 elements of the Periodic Table and any combination thereof.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Amination reaction of lower aliphatic alcohols with compounds having amine functionality in the presence of zeolites, metals or their compositions is well known.

When zeolite is solely employed, the reaction is always performed at high temperature. For example, U.S. Pat. No. 4,082,805 teaches an amination reaction of $C_1$-$C_5$ alcohol or ether with ammonia in the presence of a catalyst comprising a crystalline aluminosilicate having the structure of ZSM-5 ZSM-11 or ZSM-21. The reaction temperature is between about 300-500° C., which not only results in dehydration of alcohols and therefore creates more by-products, but also increases industrial cost likes more consumption of energy, higher requirement for equipment.

Noble metals are conventional catalysts for above mentioned amination reaction. However, the selectivity is difficult to be controlled. Specifically, selectivity of primary amine which produced from lower aliphatic alcohols is quite low. Although, WO 201459574 discloses ordered porous manganese-based octahedral molecular sieves comprising some noble metals like Pd, Pt, Ru, Os, Ir, Ag, Au or a mixture. The molecular sieves mentioned won't contribute to the selectivity control of alkylamines since they are not conventional zeolites.

Zeolites comprising metals has drawn lots of research interest. U.S. Pat. No. 4,918,234 discloses an improvement in a process for producing $C_2$-$C_4$ alkylamines by the reaction of $C_2$-$C_4$ with ammonia in the zeolite catalyst which has a predominate proportion of the cations replaced with cobalt or nickel ions. However, hydrogen is inevitably used to ensure the selectivity.

U.S. Pat. No. 3,384,667 discloses using crystalline aluminosilicate catalyst having pores of a size to selectively yield primary and secondary amines. Cations of zeolites may be replaced by metals of Groups 1, 2, 3, 11 and 12 of the Periodic Table. Nevertheless, the selectivity of primary amine is almost equal to that of secondary amine.

INVENTION

It is therefore an objective of this invention to provide an effective process for converting alcohols to corresponding primary or secondary amines, with desired characteristics such as inexpensiveness, high selectivity and conversion, ease of handling and overcome the drawbacks in prior arts. Specifically, it becomes possible to produce high selectivity of primary amines with high conversion through shape selectivity via the intercrystalline pores of the crystalline aluminosilicate zeolite catalyst, notably at low temperatures without substantial conversion to by-product nitrile, olefin.

The present invention concerns then a process for forming a primary or a secondary amine, comprising reacting:

A first reactant having 5-30 carbon atoms and one or two primary hydroxyl functionalities, with A second reactant being $NH_3$ or a reactant having primary amine functionality, in the presence of at least one zeolite comprising a transition metal chosen in the group consisting of Group 8 to 12 elements of the Periodic Table and any combination thereof.

The present invention also concerns a zeolite comprising a transition metal chosen in the group consisting of Group 8 to 12 elements of the Periodic Table and any combination thereof. Notably, the transition metal is chosen in the group consisting of Ru, Co, Ni, Rh, Pd, Pt, Au, Cu and any combination thereof.

Other characteristics, details and advantages of the invention will emerge even more fully upon reading the description which follows.

Definitions

Throughout the description, including the claims, the term "comprising one" should be understood as being synonymous with the term "comprising at least one", unless otherwise specified, and "between" should be understood as being inclusive of the limits.

It should be noted that in specifying any range of concentration, any particular upper concentration can be associated with any particular lower concentration.

It is specified that, in the continuation of the description, unless otherwise indicated, the values at the limits are included in the ranges of values which are given.

The articles "a", "an" and "the" are used to refer to one or to more than one (i.e., to at least one) of the grammatical object of the article.

The term "and/or" includes the meanings "and", "or" and also all the other possible combinations of the elements connected to this term.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

As used herein, the terminology "(Cn-Cm)" in reference to an organic group, wherein n and m are each integers, indicates that the group may contain from n carbon atoms to m carbon atoms per group.

As used herein, the term "hydrocarbon group" refers to a group mainly consisting of carbon atoms and hydrogen atoms, which group may be saturated or unsaturated, linear, branched or cyclic, aliphatic or aromatic. Hydrocarbon groups of the present invention may be alkyl groups, alkenyl groups, alkynyl groups, aryl groups, alkylaryl groups, aryalkyl groups, heterocyclic groups, and/or alkylheterocyclic groups.

"Alkyl" as used herein means a straight chain or branched saturated aliphatic hydrocarbon. Preferably alkyl group comprises 1-18 carbon atoms. Representative saturated straight chain alkyls include methyl, ethyl, n-propyl, n-butyl, n-pentyl, and the like; while saturated branched alkyls include isopropyl, sec-butyl, isobutyl, tert-butyl, isopentyl, and the like.

"Alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbon atoms of the alkenyl group. Representative unsaturated straight chain alkenyls include ethenyl, propenyl, butenyl, pentenyl, hexenyl, heptenyl, octenyl, nonenyl, decenyl and the like.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups.

"Aryl" as used herein means a 6-carbons monocyclic or 10-carbons bicyclic aromatic ring system wherein 0, 1, 2, 3, or 4 atoms of each ring are substituted. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Cycloalkyl" as used herein means cycloalkyl groups containing from 3 to 8 carbon atoms, such as for example cyclohexyl.

"Heterocyclic" as used herein means heterocyclic groups containing up to 6 carbon atoms together with 1 or 2 heteroatoms which are usually selected from 0, N and S, such as for example radicals of: oxirane, oxirene, oxetane, oxete, oxetium, oxalane (tetrahydrofurane), oxole, furane, oxane, pyrane, dioxine, pyranium, oxepane, oxepine, oxocane, oxocinc groups, aziridine, azirine, azirene, azetidine, azetine, azete, azolidine, azoline, azole, azinane, tetrahydropyridine, tetrahydrotetrazine, dihydroazine, azine, azepane, azepine, azocane, dihydroazocine, azocinic groups and thiirane, thiirene, thiethane, thiirene, thietane, thiete, thietium, thiolane, thiole, thiophene, thiane, thiopyrane, thiine, thiinium, thiepane, thiepine, thiocane, thiocinic groups.

"Heterocyclic" may also mean a heterocyclic group fused with a benzene-ring wherein the fused rings contain carbon atoms together with 1 or 2 heteroatom's which are selected from N, O and S.

As used herein, the terminology "($C_n$-$C_m$)" in reference to an organic group, wherein n and m are each integers, indicates that the group may contain from n carbon atoms to m carbon atoms per group.

Should the disclosure of any patents, patent applications, and publications which are incorporated herein by reference conflict with the description of the present application to the extent that it may render a term unclear, the present description shall take precedence.

BRIEF DESCRIPTION OF DRAWINGS

FIG. 1 illustrates low pressure distillation equipment, specifically a gas-liquid-solid tri-phase reactor connected with a condense column and a collection tank in example 10. 1—gas inlet, 2—gas-liquid-solid tri-phase reactor, 3—condense column, 4—pneumatic pump, 5—gas recycle pipe, 6—collection tank, 7—outlet vent.

DETAILS OF THE INVENTION

The following examples are included to illustrate embodiments of the invention. Needless to say, the invention is not limited to described examples.

This first reactant may notably be a compound of formula (I):

$$R^1(\text{---OH})_x \qquad (I)$$

Wherein:

x is 1 or 2

$R^1$ is a straight, branched or cyclic $C_5$-$C_{30}$ hydrocarbon group $R^1$ may represent straight, branched or cyclic $C_5$-$C_{30}$ hydrocarbon group that can be an alkyl, alkenyl, aryl, cycloalkyl or heterocyclic group, eventually comprising one or several heteroatoms such as O, S, F, and N. More preferred groups for $R^1$ may be for example $C_5$-$C_{12}$ straight aliphatic hydrocarbon group, benzyl, furfuryl, and tetrahydrofurfuryl.

In addition the first reactant may comprise additional functionalities. The additional functionalities may behave as electron donating or electron withdrawing groups as long as their presence does not prevent reaction with the amine to form the imine intermediate. There is no particular limitation on the number of carbon atoms present in the reactant as long as its structure does not prevent the formation of the imine intermediate.

Preferred first reactant of the present invention, such as compounds of formula (I), is chosen in the group consisting of: 1-pentanol, 1-hexanol, 1-heptanol, 1-octanol, 1-nonanol and 1-decanol, furfuryl alcohol, 2,5-furandimethanol, 2,5-tetrahydrofuranedimethanol, benzyl alcohol, 1,6-hexandiol and 1,7-heptandiol.

This second reactant may notably be a compound of formula (II):

$$R^2\text{---}NH_2 \qquad (II)$$

Wherein:

$R^2$ is H or a straight, branched or cyclic hydrocarbon group $R^2$ may represent straight, branched or cyclic hydrocarbon group that can be an alkyl, alkenyl, aryl, cycloalkyl or heterocyclic group, eventually comprising one or several heteroatoms such as O, S, F, and N. Preferred groups for $R^2$ may be for example: H, alkyl, phenyl, benzyl, cycloalkyl, and cycloalkene. More preferred groups for $R^2$ may be H or alkyl. More preferred groups for $R^2$ may be H or $C_1$-$C_5$ alkyl.

In addition the second reactant may comprise additional functionalities. The additional functionalities may behave as electron donating or electron withdrawing groups as long as their presence does not prevent reaction with the amine to form the imine intermediate. There is no particular limitation on the number of carbon atoms present in the reactant as long as its structure does not prevent the formation of the imine intermediate.

Preferred second reactant of the present invention, such as compounds of formula (II), is chosen in the group consisting of: $NH_3$, methylamine, ethylamine and propylamine.

Optionally, hydrogen could be employed in the invented process to particularly improve the selectivity of primary amine.

The primary or secondary amine produced by the process of present invention may notably be a compound of formula (III):

Wherein:
x is 1 or 2
R¹ is a straight, branched or cyclic $C_5$-$C_{30}$ hydrocarbon group
R² is H or a straight, branched or cyclic hydrocarbon group The secondary amine produced by the process of the present invention may notably be a compound of formula (IV):

Wherein:
R¹ is a straight, branched or cyclic $C_5$-$C_{30}$ hydrocarbon group

Preferred primary or second amine of the invention, such as compounds of formula (III), is chosen in the group consisting of: 1-pentylamine, 1-hexylamine, 1-heptylamine, 1-octylamine, 1-nonylamine, 1-decylamine, benzylamine, furan-2-ylmethanamine, (tetrahydrofuran-2,5-diyl) dimethanamine, (furan-2,5-diyl) dimethanamine, 1,6-hexamethylenediamine, and 1,7-heptamethylenediamine.

Zeolites are substances having a crystalline structure and a unique ability to change ions.

In present invention, the catalyst employed in this invention may be chosen in the group consisting of an aluminosilicate zeolite, an aluminophosphate zeolite, and a gemanosilicate zeolite. There are a large number of channels or pores which interconnect to form intra-crystalline cavities. These channels, pores and cavities are often uniform or substantially uniform in size within a specific zeolite material. The dimensions of these channels, pores and cavities are such that they accept for adsorption moleculars of certain dimensions while rejecting those of larger dimensions.

It is well known that for the porous texture analysis could be performed on a gas sorption analyzer, such as Micrometrics Tristar-3020. For example, prior to the adsorption analysis, all samples were degassed under vacuum for 12 h at 623 K. Then, argon adsorption isotherm is measured at liquid argon temperature (87.45 K). Pore size distributions were calculated using nonlocal density functional theory. It could be understood by the person skilled in the art that pore size distribution reflects all the diameters of channels, pores and cavities in the zeolite. The pore diameter is the size that relates to the top point of pore size distribution (wherein the porous volume is expressed as a function of the pore size), otherwise said it is the mode of the pore size distribution or, in rare instances when the distribution is multimodal, it is the mode which, among all modes, corresponds to the highest porous volume.

Pore diameter of the zeolite ranges usually from 1.5 to 30 angstroms. In a preferred embodiment, pore diameter of the zeolite ranges from 3.0 to 13.0 angstroms. More preferably, pore diameter of the zeolite ranges from 5.0 to 8.0 angstroms.

The crystalline aluminosilicate zeolite having a predominate portion of silica to alumina molecular ratio which may be comprised between 1 and 500. Preferably, silica to alumina ratio is comprised between 5 and 300 and more preferably between 20 and 50.

Suitable zeolites are those with framework types of MFI, MEL, MTW, MFS, MRE, MWW, IMF, JRY, AFY, MTT, ATO, CAN, MEI, BEA, MOR, EON, OFF, IWV, AFR, MOZ, MSE, EMT, MAZ, FAU, AFI, LTL, SBE, SBS, SBT, USI, EZT, GME, AET, BOG, IFO, UTL, ETR, ITT, VFI or —IRY.

Examples of above mentioned zeolites with specific framework may have commodity names like ZSM-5, ZSM-11, ZSM-12, ZSM-57, ZSM-48, MCM-22, IM-5, ITQ-22, CoAPO-CJ40, CoAPO-50, ZSM-23, SAPO-31, MAPO-31, ECR-5, ZSM-18, Beta, mordenite, ECR-1, offertite, ITQ-27, CoAPO-40, CoAPSO-40, SAPO-40, ZSM-10, MCM-68, ZSM-20, ZSM-3, ZSM-4, Y, AlPO-5, SAPO-5, zeolite L, UCSB-8X (X═Co, Zn), IM-6, EMM-3, gmelinite, AlPO-8, MCM-37, boggsite, ITQ-51, IM-12, ECR-34, ITQ-33, VPI-5, MCM-9, ITQ-40. People skilled in the art can easily understand how to obtain those zeolites by preparation method reported, such as zeolite L is described in U.S. Pat. No. 4,503,023 or commercial purchase, such as ZSM available from ZEOLYST. Among these, preferred zeolites are ZSM-5, Beta, zeolite Y and mordenite.

It is preferable that H-form zeolites are used in present invention. Cations in zeolites such as Na could be replaced by hydrogen to convert the zeolite into the H-form. People skilled in the art can easily know the method to get H-form, such as the way taught by JAMES A. KADUK et. al THE RIGAKU JOURNAL, 1995 (Vol. 12, No. 2) 14-34.

The transition metal may be preferably chosen in the group consisting of: Ru, Co, Ni, Rh, Pd, Pt, Au, Cu and any combination thereof. More preferably the metal transition is chosen in the group consisting of: Ru, Rh, Pd and Co.

The preferable method to prepare zeolite comprising a transition metal chosen in the group consisting of Group 8 to 12 elements of the Periodic Table and any combination thereof is in-situ synthesis or post-treatment such as impregnation, ion-exchange.

The loading amount of transition metal on zeolite is comprised between 0.5% and 30% by weight, preferably between 5% and 10% by weight.

The weight ratio of zeolite comprising a transition metal chosen in the group consisting of Group 8 to 12 elements of the Periodic Table and any combination thereof to first reactant is comprised between 1% and 30%, preferably between 5% and 20%.

The invented process might be performed at a temperature and for a time sufficient for the primary amine or the secondary amine to be produced.

In one embodiment, the so prepared amine is or includes a primary amine and the selectivity of the primary amine is preferably of at least 40% and preferably is comprised from 40% to 95% and more preferably from 80% to 95%.

The reaction temperature may be comprised between 120 and 280° C., preferably between 160 and 200° C. The reaction may be carried out in liquid or gas phase. In liquid phase, the reaction may be performed in the absence or presence of a solvent. The solvent is typically chosen based on its ability to dissolve the reactants.

The solvent may be protic, aprotic or a combination of protic and aprotic solvents. Exemplary solvents include toluene, octane, xylene, benzene, n-butanol, and acetonitrile. In some embodiments the solvent is a non-polar, aprotic solvent such as toluene. Solvents comprising hydroxyl functionalities or amine functionalities may be used as long as the solvent does not participate in the reaction in place of the reactant.

The reactants, with an optional solvent, and the catalyst are typically combined in a reaction vessel and stirred to constitute the reaction mixture. The reaction mixture is typically maintained at the desired reaction temperature under stirring for a time sufficient to form the primary or the secondary amine in the desired quantity and yield.

When the reaction is performed in liquid phase, $NH_3$ and $H_2$ might be mixed and introduced into reaction medium in one embodiment. In gas phase, the reaction may be performed under a pressure comprised between 1 and 100 bars.

The reaction may be carried out in the presence of air but preferably with an inert atmosphere such as $N_2$, Ar, $CO_2$. Those atmospheres may be introduced to the reaction mixture solely or in a form of mixture with $NH_3$ and/or $H_2$.

The catalyst is typically removed from the reaction mixture using any solid/liquid separation technique such as filtration, centrifugation, and the like or a combination of separation methods. The product may be isolated using standard isolation techniques, such as distillation.

In addition, the catalyst can be reused. If desired, the catalyst can be regenerated by washing with methanol, water or a combination of water and methanol and subjecting the washed catalyst to a temperature of about 100° C. to about 500° C. for about 2 to 24 hours in the presence of oxygen.

This reaction of present reaction may be conducted on any conventional equipment suitable to effect production of amines. This reaction may be carried out either batchwise or continuously. Preferably, the reaction is carried out in a continuous mode.

In a preferred embodiment, the reaction of present invention could be conducted on a low pressure distillation equipment, specifically a gas-liquid-solid tri-phase reactor connected with a condense column and a collection tank, as notably shown in FIG. 1. The gas pressure in this equipment could be comprised between 0 barg and 10 barg and more preferably between 0 barg and 3 barg. The primary amine could be continuously separated from the reaction medium by distillation and may have a selectivity of at least 85%, especially in the reaction of 1-octanol and $NH_3$.

The invention is further illustrated by the following non-limiting examples.

EXPERIMENTAL PART

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1: Catalyst Preparation

H-Beta (Si/Al=25 mol ratio, H-Beta, pore diameter 6.6 angstroms, Clariant) 1 g was impregnated by 5 wt % Ru using incipient-wetness method in an aqueous solution that contains 0.2 g $H_2O$ and 0.1024 g $RuCl_3.xH_2O$. The mixture was stirred at room temperature for 2 h and then it was dried at 80° C. overnight and calcined in air at 400° C. for 2 h.

Example 2: Catalyst Preparation

H-Beta (Si/Al=25 mol ratio, H-Beta, pore diameter 6.6 angstroms, Clariant) 1 g was impregnated by 10 wt % Ru using incipient-wetness method in an aqueous solution that contains 0.2 g $H_2O$ and 0.2048 g $RuCl_3.xH_2O$. The mixture was stirred at room temperature for 2 h and then it was dried at 80° C. overnight and calcined in air at 400° C. for 2 h.

Example 3: Catalyst Preparation

HY (Si/Al=20 mol ratio, HY, pore diameter 7.4 angstroms, Nankai zeolite) 1 g was impregnated by 5 wt % Ru using incipient-wetness method in an aqueous solution that contains 0.2 g $H_2O$ and 0.1024 g $RuCl_3.xH_2O$. The mixture was stirred at room temperature for 2 h and then it was dried at 80° C. overnight and calcined in air at 400° C. for 2 h.

Example 4: Catalyst Preparation

H-Beta (Si/Al=25 mol ratio, H-Beta, pore diameter 6.6 angstroms, Clariant) 1 g was impregnated by 5 wt % Ni using incipient-wetness method in an aqueous solution that contains 0.2 g $H_2O$ and 0.2507 g $Ni(NO_3)_2.6H_2O$. The mixture was stirred at room temperature for 2 h and then it was dried at 80° C. overnight and calcined in air at 400° C. for 2 h.

Example 5: Synthesis of Amines

The catalytic reaction in liquid phase was carried out in a sealed 30-mL autoclave. 150 mg catalyst Example 1 was pre-reduced by 20 mL/min $H_2$ at 180° C. for 2 h. The mol ratio is 1-octanol:$NH_3$:$H_2$=1:10:6. After 16 h reaction under 180° C., it resulted 63% conversion of 1-octanol, in which 99% selectivity of primary amine and 1% selectivity of secondary amine.

Example 6: Synthesis of Amines

The catalytic reaction in liquid phase was carried out in a sealed 30-mL autoclave. 150 mg catalyst Example 2 was pre-reduced by 20 mL/min $H_2$ at 180° C. for 2 h. The mol ratio is 1-octanol:$NH_3$:$H_2$=1:10:12. After 16 h reaction under 180° C., it resulted 80% conversion of 1-octanol, in which 95% selectivity of primary amine and 5% selectivity of secondary amine.

Example 7: Synthesis of Amines

The catalytic reaction in liquid phase was carried out in a sealed 30-mL autoclave. 150 mg catalyst Example 3 was pre-reduced by 20 mL/min $H_2$ at 180° C. for 2 h. The mol ratio is 1-octanol:$NH_3$:$H_2$=1:10:12. After 16 h reaction under 180° C., it resulted 93% conversion of 1-octanol, in which 85% selectivity of primary amine, 9% selectivity of secondary amine and 6% selectivity of olefins.

Example 8: Synthesis of Amines

The catalytic reaction in liquid phase was carried out in a sealed 30-mL autoclave. 150 mg catalyst Example 4 was pre-reduced by 20 mL/min $H_2$ at 400° C. for 2 h. The mol ratio is 1-octanol:$NH_3$:$H_2$=1:10:12. After 16 h reaction under 180° C., it resulted 10% conversion of 1-octanol, in which 94% selectivity of primary amine, 4% selectivity of secondary amine, 1% selectivity of olefins and 1% selectivity of heptyl cyanide.

Comparative Example 9

This comparative example is performed by using classic catalyst 5% Ru/C Johnson Matthey and catalyst obtained by Example 1 under the same reaction conditions of Example 5. Catalyst performance over two catalysts is reported in Table 1.

It appears catalyst of the present invention show excellent performance on selectivity specifically for primary amine in comparison with classic catalyst.

TABLE 1

| | OCO conv/% | 1st amine selec. % | 2nd amine selec. % | 3rd amine selec. % |
|---|---|---|---|---|
| 5% Ru/C | 100 | 21 | 75 | 4 |
| 5% Ru/Beta(Si/Al = 25 mol ratio) | 63 | 99 | 1 | 0 |

Example 10: Catalyst Preparation $RuCl_3$ precursor 5.30 g is dissolved in $H_2O$ 500 g, H-Beta (Si/Al=25 mol ratio, H-Beta, pore diameter 6.6 angstroms, Clariant) 50 g is added into the Ru precursor aqueous solution, with a stirring at 20° C., for 16 h. Then the mixture was heated to 60° C. and kept stirring. NaOH aqueous solution (10 wt %) is used to tune the pH of mixture and dropwise added till pH=7.4±0.1. The mixture is stirred at 60° C. for 20 h, and then kept static for 16 h. In the end, the solid is filtered and washed by $H_2O$ and acetone and then the solid cake is dried at 80° C. for 20 h.

Example 11: Synthesis of Amines on a Low Pressure Distillation Equipment 400 g 1-octanol and 40 g catalyst of EXAMPLE 1 was loaded in the gas-liquid-solid tri-phase reactor 2 firstly. Valve of gas inlet 1 was opened to increase $N_2$ pressure till 1 barg and then closed. Valve of outlet vent 7 was then opened to decrease pressure till 0 barg. This $N_2$ replacement was performed for 3 times at room temperature in aim of oxygen removal. Temperature was then increased to 130° C. at a constant stirring speed of 1000 rpm.

When temperature reached at 130° C., valve of gas inlet 1 was opened to increase $H_2$ pressure till 1 barg and then closed. Valve of outlet vent 7 was opened to decrease pressure will 0 barg. This $H_2$ replacement was performed for 3 times in aim of $N_2$ removal. $H_2$ was fed in reactor through deep pipe connected with a filter. To start catalyst activation procedure, temperature was increased from 130° C. to 180° C. in 50 minutes. The pneumatic pump 4 was run at a flow rate of around 10-12 L/min. During this catalyst activation procedure, the pressure was kept around 1 barg.

After finishing catalyst activation, $NH_3$ gas was fed into the reactor through gas inlet 1. Reaction temperature was maintained at 180° C. The pressure was controlled under 2 barg. $NH_3$ gas, water vapor, organic vapor was simultaneously pumped out of reactor by pneumatic pump 4. Those vapors went into the condense column 3 which was cooled by atmosphere. Water vapor and organic vapor condensate was collected in collection tank 6. $NH_3$ gas was re-pumped and re-injected into the reactor through a gas recycle pipe 5.

In the collection tank 6, the liquid phase can be found. The bottom aqueous phase contains mainly water, ammonia and small amount of 1-octylamine, 1-octanol. The upper layer is organic phase which is analyzed by GC, which contained 1-octylamine, Di-octylamine, heptyl cyanide and 1-octanol. The selectivity of 1-octylamine is 88.5%. The selectivity of Di-octylamine is 5.7%. The selectivity of heptyl cyanide is 5.7%.

The invention claimed is:

1. A process for forming a primary or a secondary amine, comprising reacting:
   A first reactant having 5-30 carbon atoms and one or two primary hydroxyl functionalities, with
   A second reactant being $NH_3$ or a reactant having primary amine functionality,
   in the presence of at least one zeolite comprising a transition metal selected from the group consisting of Ru, Rh, Pd, and any combination thereof, and
   wherein the reaction is conducted on a gas-liquid-solid tri-phase reactor connected with a condense column and a collection tank, and wherein the gas pressure is from 0 barg to 10 barg.

2. The process according to claim 1, wherein the first reactant is a compound of formula (I):

$$R^1(-OH)_x \quad (I)$$

Wherein:
   x is 1 or 2
   $R^1$ is a straight, branched or cyclic $C_5$-$C_{30}$ hydrocarbon group.

3. The process according to claim 2, wherein $R^1$ is selected from the group consisting of: $C_5$-$C_{12}$ straight aliphatic hydrocarbon group, benzyl, furfuryl and tetrahydrofurfuryl.

4. The process according to claim 3, wherein the first reactant is selected from the group consisting of: 1-pentanol, 1-hexanol, 1-heptanol, 1-octanol, 1-nonanol, 1-decanol, furfuryl alcohol, 2,5 furandimethanol, 2,5-tetrahydrofuranedimethanol, benzyl alcohol, 1,6-hexandiol and 1,7-heptandiol.

5. The process according to claim 1, wherein the second reactant is a compound of formula (II):

$$R^2-NH_2 \quad (II)$$

Wherein:
   $R^2$ is H or a straight, branched or cyclic hydrocarbon group.

6. The process according to claim 5, wherein $R^2$ is H or $C_1$-$C_5$ alkyl.

7. The process according to claim 1, wherein the primary or secondary amine produced is a compound of formula (III):

$$R'(-NHR^2)_x \quad (III)$$

Wherein:
   x is 1 or 2
   le is a straight, branched or cyclic $C_5$-$C_{30}$ hydrocarbon group
   $R^2$ is H or a straight, branched or cyclic hydrocarbon group.

8. The process according to claim 1, wherein a secondary amine is produced and is a compound of formula (IV):

$$R^1{}_2NH \quad (IV)$$

Wherein:
   $R^1$ is a straight, branched or cyclic $C_5$-$C_{30}$ hydrocarbon group.

9. The process according to claim 1, wherein the primary amine or secondary amine produced is selected from the group consisting of: 1-pentylamine, 1-hexylamine, 1-heptylamine, 1-octylamine, 1-nonylamine and 1-decylamine, benzylamine, furan-2-ylmethanamine, (tetrahydrofuran-2,5-diyl) dimethanamine, (furan-2,5-diyl) dimethanamine, 1,6-hexamethylenediamine, and 1,7-heptamethylenediamine.

10. The process according to claim 1, wherein the process comprises a third reactant being hydrogen.

11. The process according to claim 1, wherein the molecular ratio of silica/alumina in zeolite is comprised between 5 and 300.

12. The process according to claim 1, wherein the zeolite is selected from the group consisting of: ZSM-5, Beta, zeolite Y and mordenite.

13. The process according to claim 1, wherein the loading amount of transition metal on zeolite is between 5% and 10% by weight.

14. The process according to claim 1, wherein the weight ratio of zeolite comprising a transition metal selected from the group consisting of Ru, Rh, Pd, and any combination thereof to first reactant is between 5% and 20% by weight.

15. The process according to claim 1, wherein the reaction temperature is between 120 and 280° C.

* * * * *